(12) United States Patent
Kakiuchi et al.

(10) Patent No.: US 8,486,246 B2
(45) Date of Patent: Jul. 16, 2013

(54) REFERENCE ELECTRODE COATED WITH IONIC LIQUID AND ELECTROCHEMICAL MEASUREMENT SYSTEM USING THE REFERENCE ELECTRODE

(75) Inventors: Takashi Kakiuchi, Wakayama (JP); Satoshi Nomura, Kyoto (JP); Mikito Yamanuki, Kyoto (JP); Yasukazu Iwamoto, Kyoto (JP); Manabu Shibata, Osaka (JP)

(73) Assignee: HORIBA, Ltd., Kyoto-shi (JP)

( * ) Notice: Subject to any disclaimer, the term of this patent is extended or adjusted under 35 U.S.C. 154(b) by 417 days.

(21) Appl. No.: 12/441,370

(22) PCT Filed: Sep. 13, 2007

(86) PCT No.: PCT/JP2007/067856
§ 371 (c)(1),
(2), (4) Date: Mar. 23, 2009

(87) PCT Pub. No.: WO2008/032790
PCT Pub. Date: Mar. 20, 2008

(65) Prior Publication Data
US 2009/0283404 A1 Nov. 19, 2009

(30) Foreign Application Priority Data
Sep. 13, 2006 (JP) .................. 2006-248772

(51) Int. Cl.
*G01N 27/26* (2006.01)
(52) U.S. Cl.
USPC ........... 204/435; 204/416; 204/418; 204/420; 204/433

(58) Field of Classification Search
USPC .................. 204/435, 416, 418, 419, 420, 433
See application file for complete search history.

(56) References Cited

FOREIGN PATENT DOCUMENTS

| CN | 1059092 A | 3/1992 |
|---|---|---|
| JP | 11258197 | 9/1999 |
| JP | 2001-289812 | 10/2001 |
| JP | 2004-045279 | 2/2004 |
| JP | 2007064971 | 3/2007 |

OTHER PUBLICATIONS

Takashi Kakiuchi and Takahiro Yoshimatsu, A New Salt Bridge Based on the Hydrophobic Room-Temperature Molten Salt, Bull. Chem. Soc. Jpn. vol. 79, No. 7, 1017-1024, Jul. 4, 2006.*
Amir Saheb, Jiri Janata, Mira Josowicz, Reference Electrode for Ionic Liquids, Electroanalysis 18, Feb. 15, 2006, 405-409.*
Li et al., Rheological Images of Poly(vinyl chloride) Gels 1. The Dependence of Sol-Gel Transition on Concentration, Macromolecules, 30, 7835-7841, (1997).*

(Continued)

*Primary Examiner* — Luan Van
*Assistant Examiner* — Maris R Kessel
(74) *Attorney, Agent, or Firm* — Allenman Hall McCoy Russell & Tuttle LLP

(57) ABSTRACT

This invention provides a reference electrode that can be downsized and stable in voltage. The reference electrode in accordance with this invention is a reference electrode that does not require an internal aqueous solution such as a KCl aqueous solution and comprises a metal body, a slightly soluble salt film that comprises a slightly soluble salt of the metal body and that coats the metal body and a hydrophobic ionic liquid that is arranged to make contact with both the slightly soluble salt film and a sample to be measured.

9 Claims, 18 Drawing Sheets

OTHER PUBLICATIONS

Maminska, R. et al., "All-solid-state Miniaturised Planar Reference Electrodes Based on Ionic Liquids", Sensors and Actuators B 115, 552-557, Jul. 21, 2005.

Yoshimatsu, T. et al., "Stability of the Phase-Boundary Potential between a Reference Electrode coated with a Hydrophobic Ionic Liquid and an Aqueous Solution", The Electrochemical Society of Japan Shuki Taikai Koen Yoshishu; p. 244; Sep. 14, 2006.

Shibata, M. et al.,"Basic Examination on Reference Electrode for measuring Electric Potential by the use of Ionic Liquid Salt Bridge", The Japan Society for Analytical Chemistry Dai 55 Nenkai Koen Yoshishu, p. 162; Sep. 6, 2006.

Japanese Patent Office, International Search Report of PCT/JP2007/067856, Oct. 30, 2007, 2 pages, JPO.

Seddon, K. et al., "Influence of Chloride, Water, and Organic Solvents on the Physical Properties of Ionic Liquids," Pure Appl. Chem., vol. 72, No. 12, pp. 2275-2287, Jul. 2000, 13 pages.

Wei, D. et al., "Applications of Ionic Liquids in Electrochemical Sensors," Laboratory of Analytical Chemistry, Abo Akademi University, Finland, Dec. 23, 2007, 10 pages.

* cited by examiner

REFERENCE ELECTRODE COATED WITH IONIC LIQUID AND ELECTROCHEMICAL MEASUREMENT SYSTEM USING THE REFERENCE ELECTRODE

FIELD OF THE ART

This invention relates to a reference electrode that can be a reference for calculation or measurement of an electrode potential and an electrochemical measurement system using the reference electrode.

BACKGROUND ART

Presently most extensively used reference electrodes (comparison electrode) such as silver/silver chloride electrodes (Ag/AgCl electrode) or calomel electrodes (Hg/$Hg_2Cl_2$) are used to generate a stable potential by immersing an electrode comprising a metal body and a slightly soluble salt film that covers the metal body and that is made of slightly soluble salt to the metal in an aqueous solution comprising an anion constituting the slightly soluble salt such as, for example "chloride salt ion ($Cl^-$), and are referred to herein as reference electrodes based on a second electrode principle. The potential of such a reference electrode is stable, however, since the potential depends on the $Cl^-$ concentration in the internal aqueous solution, it is necessary to keep the concentration constant. In addition, a salt bridge is required in order to prevent the internal aqueous solution from directly attaching the sample solution and to keep the liquid junction potential constant.

For the above-mentioned reference electrode, the KCl aqueous solution is used as the internal aqueous solution, and in order to minimize the fluctuation of the liquid junction potential between the internal aqueous solution and the sample solution, the internal electrode comprising Ag/AgCl or $Hg/Hg_2Cl_2$ or the like is immersed into the internal aqueous solution comprising a KCl aqueous solution of high concentration (3.3 M (M=mol/$dm^3$)~saturation) so that the internal aqueous solution makes contact with the sample solution through a junction comprising a porous body such as ceramics or glass. (Refer to, for example, patent document 1).

However, if the KCl solution of high concentration is used as the internal aqueous solution of the reference electrode, there are problems; the sample solution is polluted because the $K^+$ and $Cl^-$ move to a side of the sample solution on a constant basis so that KCl elutes out into the sample solution, and there is a need to frequently fill in or exchange the internal aqueous solution because the KCl concentration of the internal aqueous solution decreases. In addition, there is another problem that an accurate measurement is hindered because the AgCl dilutes from the internal electrode and deposits and attaches inside a pore of the junction so that the junction is clogged. Furthermore, for a reference electrode using an internal aqueous solution, there is a problem that it is difficult to downsize the reference electrode because it is necessary to consider the volatility of the internal aqueous solution in designing the reference electrode and, for example, to enlarge a capacity to accommodate the internal aqueous solution.

Meanwhile, there is an attempt to gelatinize the internal aqueous solution or to cover the internal aqueous solution by an electroconductive polymer, however, nothing can be comparable to the reference electrode using the internal aqueous solution in stability and repeatability of potential.

Recently the present inventors invented a salt bridge using slightly soluble ionic liquid. By the use of a reference electrode using the salt bridge, it is possible to almost completely remove the fluctuation of the electric potential difference at the junction, to minimize the pollution in the sample solution, to lessen frequency of filling in and exchanging the internal aqueous solution, to prevent clogging at the junction, to maintain the durability of the reference electrode for a long time and to conduct measurement with high accuracy.

However, since this reference electrode still uses the internal aqueous solution, there is a problem that it is difficult to downsize the reference electrode because it is necessary to consider the volatility of the internal aqueous solution in designing the reference electrode as mentioned above.

In addition, there is a planate reference electrode wherein a surface of an Ag/AgCl electrode is coated with a PVC (polyvinyl chloride) film comprising an ionic liquid as shown in non-patent document 1.

In non-patent document 1, for an ionic liquid impregnated solid PVC electrode, a $Cl^-$ ion is an anion for both the ionic liquid and the ion-exchange material and a Nernst response is expected for the $Cl^-$ ion in the solution. In addition, generally such a result was shown (refer to non-patent document FIG. 2~FIG. 5). As a result, since this electrode does not have a function of salt bridge, it is not possible to use the electrode by itself for a pH measurement method using a potentiometer measurement method (potentiometry) wherein a glass electrode is combined with a reference electrode having a salt bridge. In addition, it is not possible to use an electrode by itself also for other potentiometry, and there is a problem that the salt bridge has to be combined.

Patent document 1: Japan Patent Laid-open number 11-258197

Non patent document 1: MAMINSKA Renata, etc. All-solid-state miniaturized planar reference electrodes based on ionic liquids, Sensors and Actuators B, number 115, p. 552-557, May 23, 2006

DISCLOSURE OF THE INVENTION

Problems to be Solved by the Invention

The present claimed invention intends to solve all of these problems and its main object is to provide a reference electrode that has a merit of a salt bridge using the hydrophobic ionic liquid, that can stabilize a voltage in a short period of time and that can be downsized.

Means to Solve the Problems

More specifically, a reference electrode in accordance with this invention is characterized by comprising a metal body, a slightly soluble salt film that comprises a slightly soluble salt of the metal which constitutes the metal body and that coats at least a part of the metal body, and hydrophobic ionic liquid that is arranged to make contact with both the slightly soluble salt film and a sample to be measured. The phrase, "the hydrophobic ionic liquid that is arranged to make contact with both the slightly soluble salt film and a sample to be measured" means a physical contact, for example, the metal body coated with the slightly soluble salt film is immersed in the hydrophobic ionic liquid, or the slightly soluble salt film is further coated with the hydrophobic ionic liquid. In addition, "hydrophobic ionic liquid", details of which will be described later, comprises a combination of an organic or inorganic cation and an organic or inorganic anion, and mainly means hydrophobic salt with a solubility in water that is about several mM (mmol/$dm^3$) or less. The ionic liquid is also referred to as an ion liquid or molten salt at a normal temperature.

The ionic liquid is salt in a molten state at a normal temperature. If a cation and an anion constituting the ionic liquid are fully hydrophobic, the ionic liquid will not be mixed with water and an ionic liquid phase separated from an aqueous phase is formed. As a result, if an aqueous solution makes contact with a hydrophobic ionic liquid, a hydrophilic ion contained in the aqueous solution cannot move into the hydrophobic ionic liquid. Although ions constituting the hydrophobic ionic liquid move (distribute) into the aqueous solution, the amount of the ions moving into the aqueous solution is small (small in distribution coefficient to water) and a distribution equilibrium state is immediately formed near an interface.

The present claimed invention is completed with focusing attention on a property of the hydrophobic ionic liquid, and the hydrophobic ionic liquid is used as a means to make the internal aqueous liquid of the reference electrode unnecessary. For a conventional reference electrode wherein a KCl solution of high concentration is used as an internal aqueous solution and the KCl solution directly contacts the sample solution, a fluctuation of an electric potential difference between the internal aqueous solution and the sample solution is restricted due to a one-way movement of $K^+$ and $Cl^-$ from the internal aqueous solution to the sample solution.

On the contrary, in the case that the hydrophobic ionic liquid is arranged to make contact with the metal body as being an internal electrode through the slightly soluble salt film without using an internal aqueous solution, an amount of the ions constituting the hydrophobic ionic liquid that moves into the sample solution is extremely small.

As a result, it is possible for the reference electrode in accordance with this invention to minimize pollution of the sample solution and to almost completely remove problems, which a conventional reference electrode faces, of a liquid junction potential difference between an internal aqueous solution and a sample solution due to the internal aqueous solution. In addition, it is possible to omit maintenance work such as filling up or exchanging the internal aqueous solution periodically. Furthermore, since there is no need of a conventional liquid junction comprising a porous body, it is possible to prevent the metal salt that might elute from the metal body from depositing on or attaching to a pore. In addition, it is possible to suppress an eluting speed to be extremely slow so that pollution of the sample solution can be prevented.

Furthermore, since a hydrophobic ionic liquid with a volatility that is extremely small is used without using an internal aqueous solution such as a KCl solution with a volatility that is large, there is no need to design the reference electrode with consideration of the volatility of the internal aqueous solution, enabling downsizing of the reference electrode. In addition, since the hydrophobic ionic liquid is arranged to make contact with the slightly soluble salt film and the sample solution, it is possible to stabilize the electric potential in a short period of time and to hasten the responsiveness. Furthermore, since the solubility in water is about several mM or less, it is possible to suppress pollution of the sample solution.

A concrete example of the hydrophobic ionic liquid represented is a hydrophobic ionic liquid comprising a cation and an anion for which standard Gibbs energy transferring between an ionic liquid and water is almost the same. "The standard Gibbs energy transferring between an ionic liquid and water" refers to the Gibbs (free) energy that is necessary for the cation and the anion constituting the ionic liquid to transfer between the ionic liquid and water in a standard state. In addition, "almost the same" may mean almost the same level in the order. The hydrophobic ionic liquid indicates an ionic liquid wherein a sum of the standard Gibbs energy of the cation constituting the hydrophobic ionic liquid transferring between the ionic liquid and water and that of the anion constituting the hydrophobic ionic liquid is about 30 kJ/mol or less in a standard state (0.1 MPa at 25° C.). The ionic liquid that satisfies this condition is a kind of a slightly soluble salt that shows a property of being insoluble in water. The following is presented as a concrete example of a cation and anion in which standard Gibbs energy transferring between the ionic liquid and water is almost the same.

As the cation represented is at least one or more of quaternary ammonium cation, quaternary phosphonium cation or quaternary alzonium cation, in more detail represented is at least one or more of $C_i$mim (1-alkyl-3-methyl imidazolium ion) (i represents a carbon number of alkyl group) such as $(C_2H_5)_4N^+$, $C_4mim^+$, $C_6mim^+$, $C_8mim^+$ and $C_{10}mim^+$, $(n-C_3H_7)_4N^+$, $(n-C_4H_9)_4N^+$ and $Ph_4As^+$.

In addition, as the anion represented is at least one or more of $[R_1SO_2NSO_2R_2]^-$ (each of $R_1$ and $R_2$ is perfluoroalkyl group with a carbon number that is 1~12 respectively), a borate ion containing fluorine, $B(CN)_4^-$ (tetracyanoborate), bis(2-ethylhexyl) sulfosuccinate, $P(C_nF_{2n+1})_3F_3^-$, $(CF_3SO_2)_3C^-$, $AsF_6^-$, $SbF_6^-$, $(C_nF_{2n+1})SO_3^-$, or $(C_nF_{2n+1})COO^-$. The hydrophobic ionic liquid comprising the cation and the anion can be used by appropriately selecting in accordance with its usage.

It is preferable that the slightly soluble salt film is contained in a saturated state in the hydrophobic ionic liquid. In accordance with this arrangement, since an equilibrium condition between each of the phases (Ag, AgCl, ionic liquid) constituting the electrode system can be secured, it is possible to secure the stability of the electric potential.

In order to facilitate handling the reference electrode and to increase the freedom of a shape of the reference electrode covered by an ionic liquid so as to make it possible to utilize the reference electrode in a field different from a conventional field by combining with another electrode, it is preferable that the hydrophobic ionic liquid is gelled. With this arrangement, the hydrophobic ionic liquid can be solidified so that it is possible to provide a reference electrode of a solid type. In addition, it is possible to effectively prevent the hydrophobic ionic liquid from eluting into the sample solution to be measured, resulting in further preventing the sample to be measured from being polluted. Furthermore, since the hydrophobic ionic liquid has a property (a shape stability) of keeping an original shape due to gelatinization, a sling tube is not necessarily required, thereby contributing to further downsizing of the reference electrode.

A method for gelatinizing the hydrophobic ionic liquid is not especially specified, however, the hydrophobic ionic liquid can be gelled by a high polymer compound. The high polymer compound is preferably gum if a sealed property to the sample solution to be measured is considered, and preferably resin if a forming facility as a covering material is considered. In addition, the high polymer compound is preferably a hydrophobic high polymer compound whose compatibility with the hydrophobic ionic liquid is high, and for example, vinylidene fluoride-hexafluoropropylene copolymer, polymethylmethacrylate, polyacrylonitrile, polybutylacrylate, and a derivative of polytetrafluoroethylene. As the derivative of polytetrafluoroethylene conceived is, for example, an amorphous fluorine resin such as Cytop (registered trademark).

As a concrete method to gelatinize the hydrophobic ionic liquid, represented is a method to obtain the gelled gelatinized hydrophobic ionic liquid by dissolving the hydrophobic ionic liquid into acetone, mixing it with vinylidene fluoride-hexafluoropropylene copolymer, and leaving it for a predetermined period of time so as to evaporate acetone.

As a concrete example of the cation, it is preferable that the cation is at least one or more of

[Chemical formula 1]

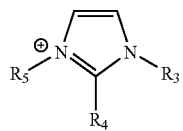
(1)

($R_3$, $R_4$, $R_5$ in the chemical formula 1 represent alkyl group with a carbon number that is 1~12, phenyl group or benzyl group. Alkyl group may contain a hetero atom.)

[Chemical formula 2]

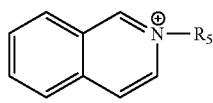
(2)

($R_6$ in the chemical formula 2 represents an alkyl group with a carbon number that is 12~18, and the alkyl group may contain a hetero atom.)

[Chemical formula 3]

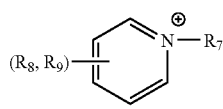
(3)

($R_7$ in the chemical formula 3 represents an alkyl group with a carbon number that is 12~18, and the alkyl group may contain a hetero atom. $R_8$, $R_9$ represent hydrogen or methyl group.)

[Chemical formula 4]

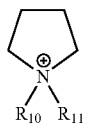
(4)

($R_{10}$, $R_{11}$ in the chemical formula 4 represent an alkyl group with a hydrogen or carbon number that is 1~12, and the alkyl group may contain a hetero atom.)

[Chemical formula 5]

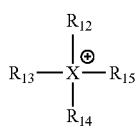
(5)

($R_{12}$, $R_{13}$, $R_{14}$, $R_{15}$ in the chemical formula 5 represent an alkyl group with a carbon number that is 1~12, a phenyl group or a benzyl group. The alkyl group may contain a hetero atom. In addition, X represents nitrogen, phosphorus or arsenic) or

[Chemical formula 6]

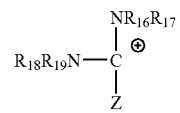
(6)

(In the chemical formula 6, $R_{16}$, $R_{17}$ represent an alkyl group with a hydrogen or carbon number that is 1~12, $R_{18}$, $R_{19}$ represent an alkyl group with a hydrogen or carbon number that is 1~12. In addition, Z represents $NR_{20}R_{21}$, $OR_{22}$ or $SR_{23}$. $R_{20}$, $R_{21}$, $R_{22}$, $R_{23}$ represent an alkyl group with a carbon number that is 1~12)

In addition, the electrochemical measurement system in accordance with this invention is characterized by comprising the above-mentioned reference electrode, namely, a reference electrode that comprises a metal body, a slightly soluble salt film that comprises a slightly soluble salt of the metal body and that coats at least a part of the metal body, and hydrophobic ionic liquid that is arranged to make contact with both the slightly soluble salt film and a sample to be measured.

In accordance with this arrangement, in addition to the effect of the above-mentioned reference electrode, if an internal electrode of an electrode for measurement (for example, a pH electrode) of the electrochemical measurement system has the same arrangement as that of the metal body and the slightly soluble salt film of the reference electrode of this invention, it is possible to cancel the electric potential change of the reference electrode and the internal electrode before and after a time when the temperature changes so that the measurement can be conducted with high accuracy.

Effect of the Invention

In accordance with this invention, it is possible to almost completely remove fluctuation originating in change of a composition of the sample solution due to an electric potential difference between the internal aqueous solution and the sample solution in case that the internal aqueous solution is used. In addition, it is possible to omit maintenance work such as filling up or exchanging the internal aqueous solution periodically. Furthermore, since there is no need of a conventional liquid junction comprising porous body, it is possible to prevent the metal salt that might elute from the metal body from depositing on or attaching to a pore. In addition, it is possible to suppress an eluting speed to be extremely slow so that pollution of the sample solution can be prevented. Furthermore, since a hydrophobic ionic liquid with a volatility that is extremely low is used without using an internal aqueous solution such as a KCl solution with a volatility that is high, there is no need of designing the reference electrode with considering volatility of the internal aqueous solution, thereby downsizing the reference electrode. In addition, since the hydrophobic ionic liquid itself has a function of a salt bridge, it is possible to downsize the reference electrode. Furthermore, a stable electric potential and quick responsiveness can be secured in addition to downsizing.

EXPLANATION OF THE REFERENCE DESIGNATORS

Figure 1:
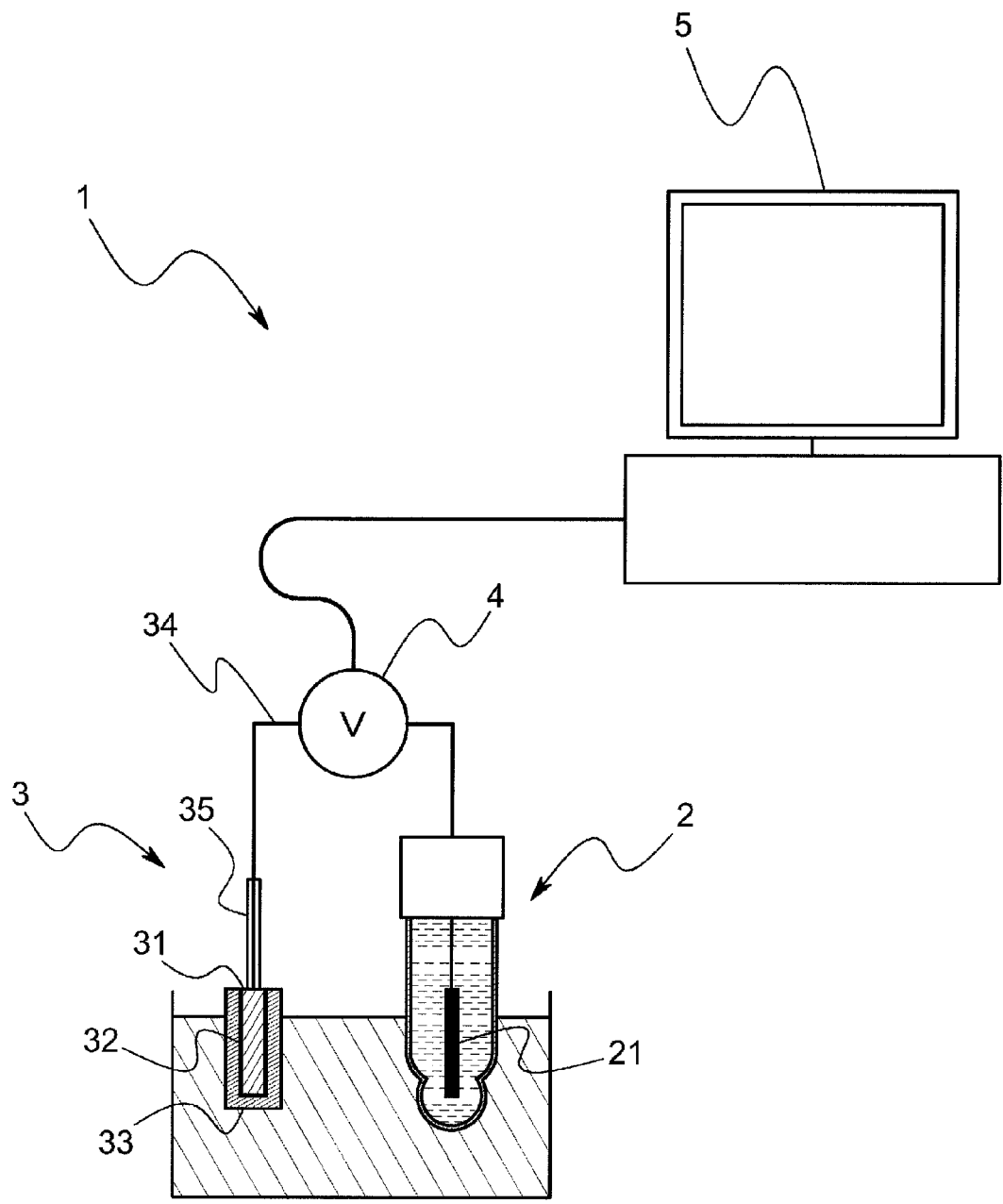
FIG. 1 is a pattern structure diagram of an ion concentration measurement system in accordance with one embodiment of the present claimed invention.

1 . . . electrochemical measurement system
2 . . . electrode for measurement
3 . . . reference electrode
31 . . . metal body
32 . . . slightly soluble salt film
33 . . . hydrophobic ionic liquid
34 . . . lead wire
4 . . . potentiometer (pH meter body)

BEST MODES OF EMBODYING THE INVENTION

One example of an electrochemical measurement system using a reference electrode in accordance with one embodiment of the present claimed invention will be explained with reference to the drawings.

<System Configuration>

The electrochemical measurement system 1 in accordance with this embodiment is, as shown in FIG. 1, an ion concentration measurement system to measure a measurement sample, such as hydrogen ion concentration (pH) in a sample solution, and comprises an electrode for measurement 2, a reference electrode 3, a potentiometer 4 that detects potential difference generating at a time when the electrode for measurement 2 and the reference electrode 3 are immersed into the sample solution, and an operational equipment 5 that calculates an ion concentration based on the potential difference detected by the potentiometer 4 and displays it. For example, purified water or low ionic strength solution such as boiler water may be preferably used as the sample solution in this embodiment.

In this embodiment, a pH electrode is used as the electrode for measurement 2. In addition to this, an ion selective electrode may be used. An internal electrode 21 of the electrode for measurement 2 uses Ag/AgCl that is the same electrode comprising a metal body 31 and a slightly soluble salt film 32 of the reference electrode 3.

Figure 2:
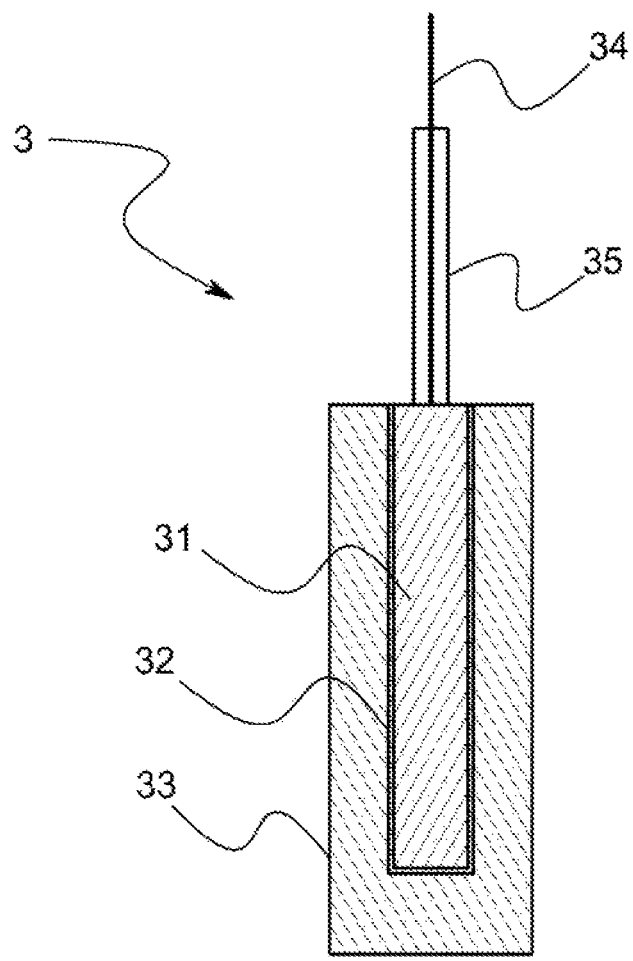
FIG. 2 is a cross-sectional view of a reference electrode in accordance with this embodiment.

The reference electrode 3 requires neither an internal aqueous solution nor a sling tube that accommodates the internal aqueous solution, as shown in FIG. 2, and comprises the metal body 31, the slightly soluble salt film 32 that covers the metal body 31, gelled hydrophobic ionic liquid 33 arranged to make contact with the slightly soluble salt film 32 and the sample solution, and a lead wire 34 that is connected to the metal body 31 so as to connect to the potentiometer 4. The reference electrode 3 can be referred to a solid type reference electrode because the hydrophobic ionic liquid 33 is gelled.

It can be conceived that, for example, silver (Ag) or mercury (Hg) is used for the metal body 31. Ag is used in this embodiment. The lead wire 34 is connected to an upper end surface of the metal body 31. The lead wire 34 extends outside and is electrically connected to the potentiometer 4. The lead wire 34 is coated with TEFLON (registered trademark) coat 35 so as to provide insulation.

The slightly soluble salt film 32 comprises metal salt of the metal which constitutes the metal body 31, the metal salt shows slightly soluble properties to the hydrophobic ionic liquid 33 and the solubility is about several mM or less. More concretely, in case that the metal body 31 is Ag, the slightly soluble salt film 32 is silver chloride (AgCl). In the case that the metal body 31 is Hg, the slightly soluble salt film 32 is mercury chloride ($Hg_2Cl_2$) or mercury sulfate ($Hg_2SO_4$). In this embodiment, the slightly soluble salt film 32 is AgCl, and a thin film that covers almost all of the surfaces of the metal body 31 except for the upper end surface.

The hydrophobic ionic liquid 33 covers the slightly soluble salt film 32 and directly contacts the sample solution. In this embodiment, the hydrophobic ionic liquid 33 covers almost all surfaces of the slightly soluble salt film 32. In addition, the hydrophobic ionic liquid 33 is gelled so as to facilitate handling and so as not to be exfoliated from the slightly soluble salt film 32 while in use.

The hydrophobic ionic liquid 33 in this embodiment comprises cations and anions with hydrophobic properties that are almost the same. In addition, in view of securing an equilibrium condition between each phase constituting an electrode system, AgCl as being the slightly soluble salt is contained in a saturated state in the hydrophobic ionic liquid 33.

As the hydrophobic ionic liquid 33 used in this embodiment, for example, representative examples are shown in the following table 1. These are one example of a combination of the cation and the anion for which standard Gibbs energy transferring between an ionic liquid and water is almost the same.

TABLE 1

| hydrophobic ionic liquid | $[C_4mim]^+$ | $[C_1C_1N]^-$ |
|---|---|---|
| | $[C_8mim]^+$ | $[C_1C_1N]^-$ |
| | $[C_8mim]^+$ | $[C_2C_2N]^-$ |
| | $[TPA]^+$ | $[C_1C_1N]^-$ |
| | $[THA]^+$ | $[C_1C_1N]^-$ |
| | $[THA]^+$ | $[C_2C_2N]^-$ |
| | $[TOA]^+$ | $[C_1C_1N]^-$ |
| | $[TBA]^+$ | $[BEHSS]^-$ |
| | $[TPA]^+$ | $[BEHSS]^-$ |
| | $[THA]^+$ | $[BEHSS]^-$ |
| | $[TOA]^+$ | $[BEHSS]^-$ |
| | $[C_{18}Iq]^+$ | $[TFPB]^-$ |
| | $[TOMA]^+$ | $[TFPB]^-$ |
| | $[THA]^+$ | $[C_3F_7BF_3]^-$ |

Each of the descriptions in Table 1 is as follows.
$[C_imim]^+$: 1-alkyl-3-methyl imidazolium ion (i represents a carbon number of alkyl group)
$[C_iC_iN]^-$: bis(perfluoroalkylsulfanilyl)imide ion (i represents a carbon number of perfluoro alkyl group)
$[TPA]^+$: tetrapentylammonium
$[THA]^+$: tetrahexylammonium
$[TOA]^+$: tetraoctylammonium
$[TBA]^+$: tetrabutylammonium
$[BEHSS]^-$: bis(2-ethylhexyl)sulfosuccinate ion
$[TFPB]^-$: tetrakis(3,5-bis(trifluoromethyl)phenyl)borate ion
$[C_{18}Iq]^+$: alkylisoquinolinium ion
$[TOMA]^+$: trioctylmetylammonium ion
$[C_3F_7BF_3]^-$: perfluoropropyltrifluoroborate ion A material to gelatinize the hydrophobic ionic liquid 33 is not especially limited, and may be represented by, for example, a chemical compound such as vinylidene fluoride-hexafluoropropylene copolymer, polymethylmethacrylate, polyacrylonitrile, polybutylacrylate, and a derivative of polytetrafluoroethylene (PTFE).

For example, the chemical compound manufactured by Sigma-Aldrich Japan may be used as the above-mentioned vinylidene fluoride-hexafluoropropylene copolymer. A method to gelatinize the hydrophobic ionic liquid 33 by the use of vinylidene fluoride-hexafluoropropylene copolymer is not especially limited, and the gelled hydrophobic ionic liquid 33 may be obtained, for example, by dissolving the hydrophobic ionic liquid 33 into acetone, mixing it with vinylidene fluoride-hexafluoropropylene copolymer (for example, Mw=400000), and leaving it overnight so as to evaporate acetone. Hardness of the gelled hydrophobic ionic liquid 33 can be varied by appropriately selecting a ratio of the hydrophobic ionic liquid 33, the copolymer and acetone, or a molecular weight of the copolymer. For example, it is possible to obtain preferably gelled hydrophobic ionic liquid 33 by making a ratio of the hydrophobic ionic liquid 33 to a total of the copolymer and acetone in volume 1 to 10.

Since the gelled hydrophobic ionic liquid 33 is not mixed with water, a solvent (water) in the sample solution and a hydrophilic ion that the solvent contains move only a little in the gelled hydrophobic ionic liquid 33. Meanwhile, although it is possible for the ion constituting the hydrophobic ionic liquid 33 to move to a side of the sample solution, an amount of the hydrophobic ionic liquid 33 that moves to the side of the sample solution is extremely small.

<Effect of this Embodiment>

With the electrochemical measurement device 1 in accordance with this embodiment, since an internal aqueous solution is unnecessary, it is possible to remove fluctuations originating in a change of a composition of the sample solution due to an electric potential difference between the internal aqueous solution and the sample solution in the case that the internal aqueous solution is used. In addition, it is possible to omit maintenance work such as filling up or exchanging the internal aqueous solution periodically. There is no need to take into consideration an effect from a pressure in a sling tube of an internal aqueous solution. Furthermore, since there is no need for a conventional liquid junction comprising a porous body, it is possible to prevent the metal salt that might elute from the metal body from depositing on or attaching to a pore. In addition, it is possible to suppress an eluting speed to be extremely slow so that pollution of the sample solution can be prevented. Furthermore, since the internal aqueous solution is unnecessary, it is possible to omit a space for the internal aqueous solution, thereby downsizing the reference electrode 3. In addition, since the hydrophobic ionic liquid is arranged to make contact with the slightly soluble salt film and the sample solution, it is possible to stabilize the electric potential in a short period of time and to hasten the responsiveness. Furthermore, since the internal electrode 21 for the measurement electrode to be inserted into the internal aqueous solution of the measurement electrode 2 has the same arrangement as that of the metal body 31 and the slightly soluble salt film 32 of the reference electrode 3, it is possible to cancel the electric potential change of the reference electrode 3 and the internal electrode 21 before and after the temperature change so that the measurement can be conducted with high accuracy.

In addition to the above, since the internal aqueous solution (for example, KCl aqueous solution) will not elute out into the sample solution such as low ionic strength solution, it is possible to prevent a pH change of the sample solution and a concentration change of a potassium ion or a chloride ion.

Furthermore, it is possible to prevent an interference with various kinds of the ion electrodes 2. With regard to, for example, a chloride ion electrode and a potassium ion electrode, it is possible to solve a problem that a measurement error is generated because $Cl^-$, $K^+$ elutes out into the sample solution and a concentration of $Cl^-$, $K^+$ as being an object ion to be measured changes. With regard to a nitrate ion electrode and a sodium ion electrode, it is possible to solve a problem that selectivity of the electrode is affected because the ion to which the nitrate ion electrode and the sodium ion electrode are sensitive is affected. Furthermore, in the case of a thiocyanic ion electrode and a copper ion electrode, it is possible to solve a problem that a measurement error is generated because the thiocyanic ion and the potassium ion forms a complex and the copper ion and the chloride ion forms a complex. In the case of a silver ion electrode, it is possible to solve a problem that the silver chloride deposits because the silver ion electrode reacts with the chloride ion.

<Embodiment 1>

Next, an embodiment 1 of measurement of the voltage between terminals by a model system using the reference electrode of the present claimed invention will be shown.

Figure 3:
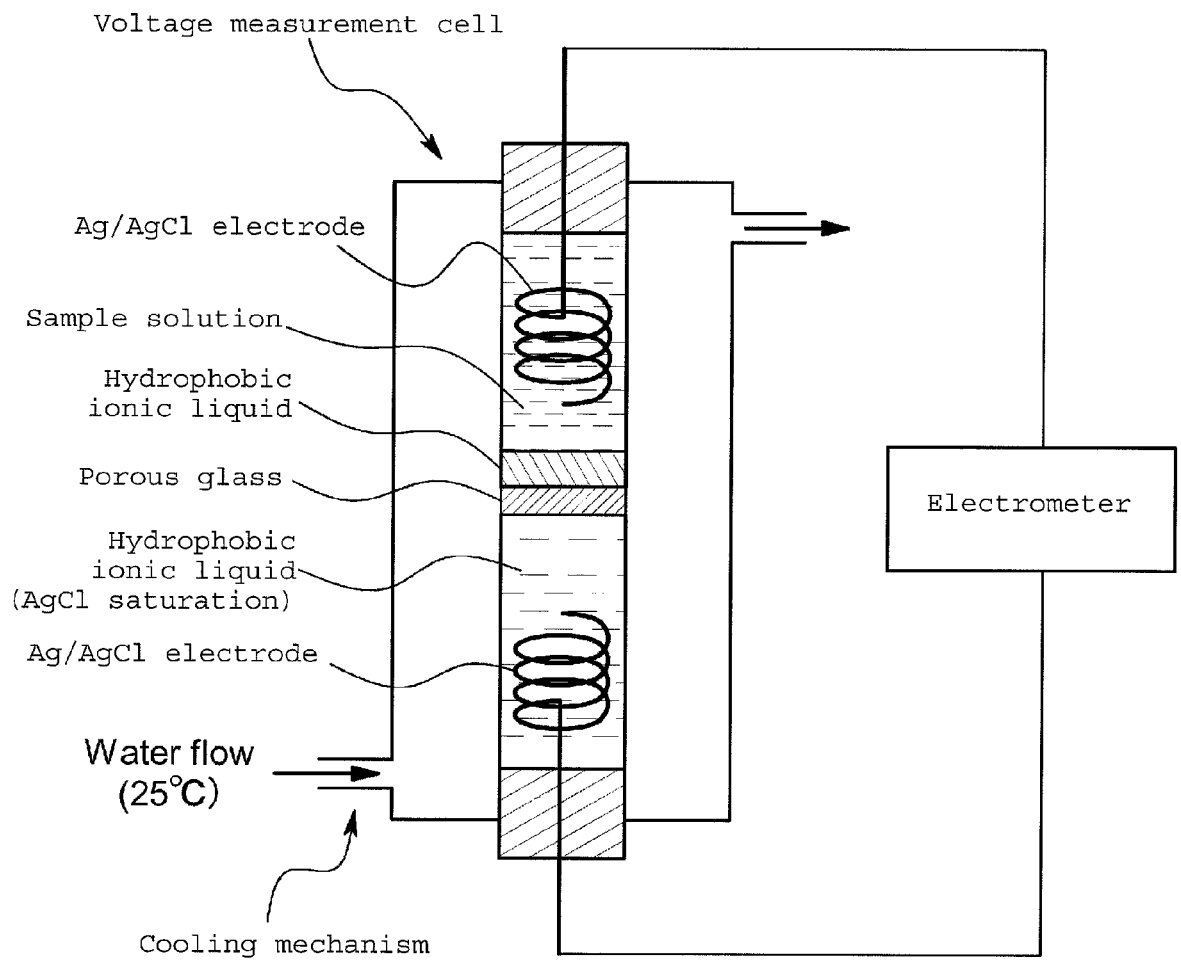
FIG. 3 is a pattern diagram showing a model system in accordance with an embodiment 1 of this invention.

The model system of this embodiment comprises, as shown in FIG. 3, a voltage measurement cell and an electrometer that measures a voltage E between terminals of the voltage measurement cell. The voltage measurement cell is so arranged that porous glass is sandwiched between a hydrophobic ionic liquid wherein silver chloride is saturated and a sample solution through a hydrophobic ionic liquid, and an Ag/AgCl electrode is inserted into the hydrophobic ionic liquid and the sample solution respectively. The model system comprises a cooling mechanism to keep the voltage measurement cell at a constant temperature (for example, 25° C.) In addition, in this embodiment, the hydrophobic ionic liquid is $C_8mimC_1C_1N$ comprising a combination of a 1-octyl-3-methyl imidazolium ion and a bis(perfluoromethylsulfanilyl) imide ion.

In accordance with the model system having the above arrangement, the voltage E between terminals was measured by changing a concentration x of the sample solution according to x=1, 2, 5, . . . , 2000 mM with the sample solution being a KCl aqueous solution.

Figure 4:
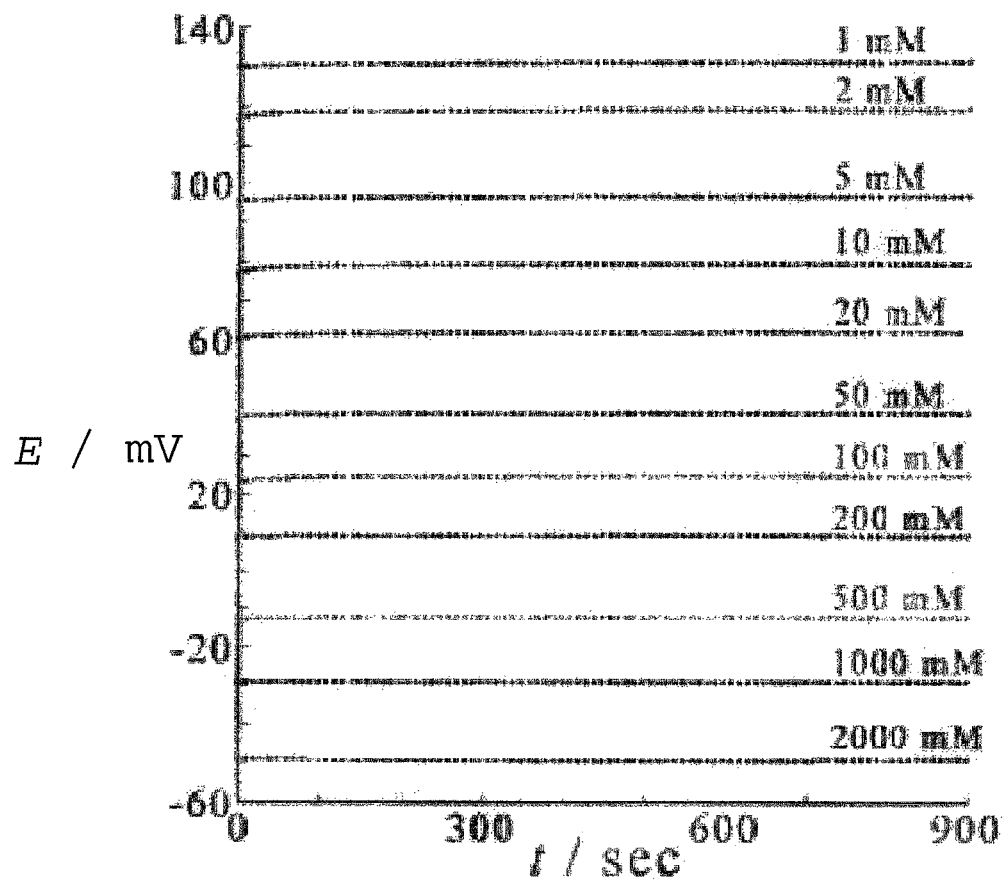
FIG. 4 is a diagram showing a time series change of a voltage between terminals recorded with changing a KCl concentration in sample solution from 1 mM to 2000 mM in this embodiment.
Figure 5:
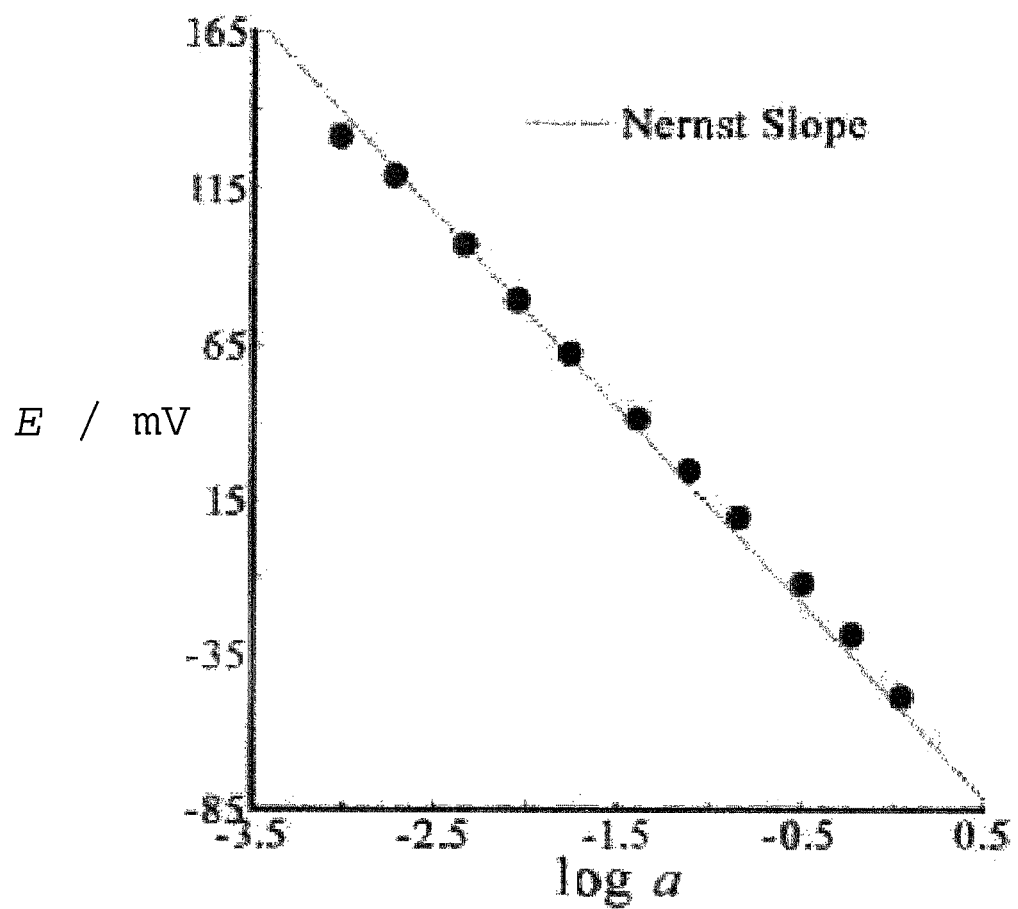
FIG. 5 is a view showing a result of the voltage between terminals, recorded by changing the KCl concentration in the sample solution from 1 mM to 2000 mM, plotted on the logarithm of an average ionic activity of the KCl concentration.

The results are shown in FIG. 4 and FIG. 5. FIG. 4 is a view showing the voltage E between terminals at a time when the concentration x of the KCl aqueous solution is changed according to x=1, 2, 5, . . . , 2000 mM, and FIG. 5 is a view showing a result of each voltage E between terminals plotted on the logarithm of an average ionic activity of KCl in the sample solution. According to FIG. 4, it turned out that the voltage E between terminals was stable in a broad range of the concentration. In addition, according to FIG. 5, it turned out that the logarithm (log a) of the ionic activity and the voltage between terminals (E) showed a linear relationship in a broad range of the ionic activity (concentration). Since the response is generated due to Ag/AgCl electrode in the sample solution making a Nernst response to the activity of Cl⁻ in the sample solution, the result showed that the voltage difference at the interface between hydrophobic ionic liquid and the sample solution was constant in a broad range of the activity of potassium chloride.

Similarly, the voltage E between terminals was measured for the concentration x of the KCl aqueous solution as being the sample solution in accordance with x=20, 50, 100, 200, 500 μM, wherein the concentration x is lower than a solubility of $C_8mimC_1C_1N$ in water.

Figure 6:
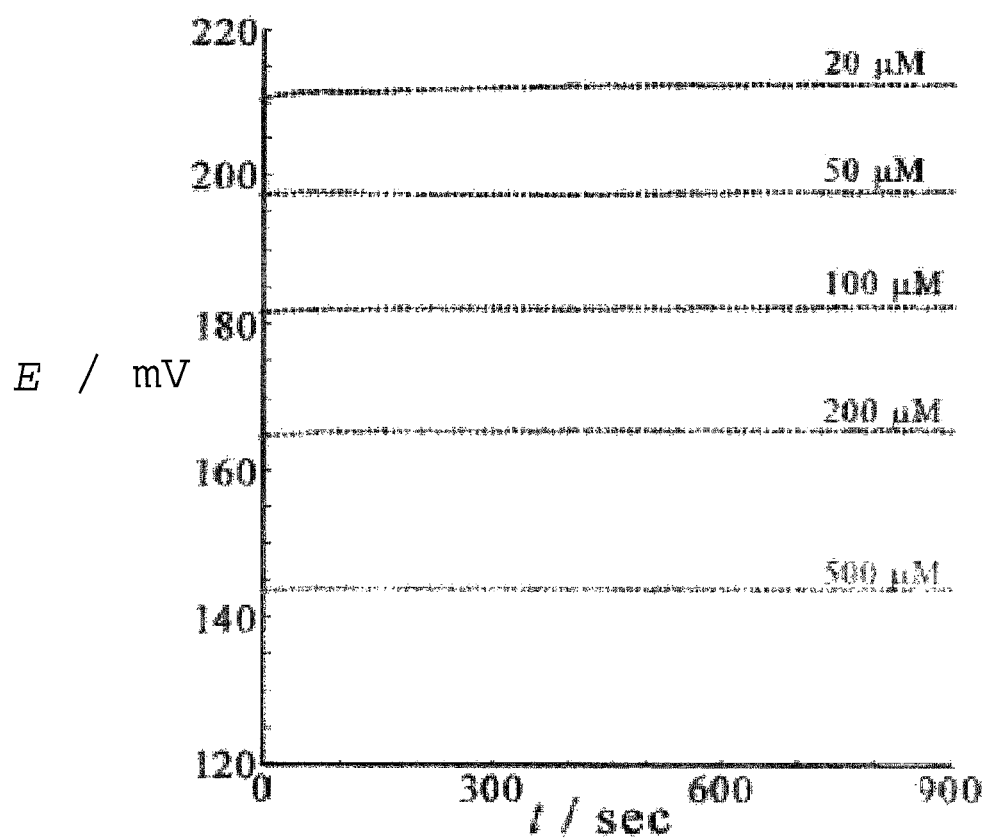
FIG. 6 is a diagram showing a time series change of the voltage between terminals recorded by changing the KCl concentration in the sample solution from 20 μM to 500 μM in this embodiment.
Figure 7:
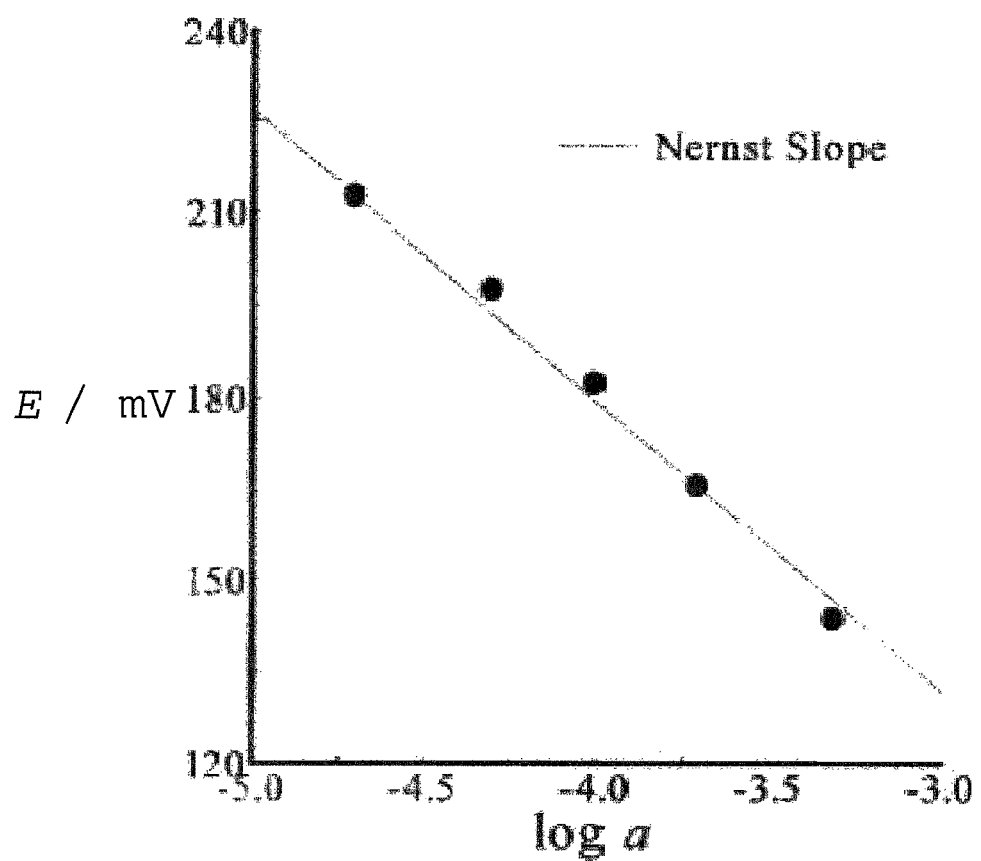
FIG. 7 is a view showing a result of the voltage between terminals, recorded by changing the KCl concentration in the sample solution from 20 μM to 500 μM, plotted on the logarithm of the average ionic activity of the KCl concentration.

The results are shown in FIG. 6 and FIG. 7. FIG. 6 is a view showing the voltage E between terminals at a time when the concentration x of the KCl aqueous solution is changed according to x=20, 50, 100, 200, 500 μM, and FIG. 7 is a view showing a result of the voltage E between terminals plotted on the logarithm of an average ionic activity of KCl in the sample solution. According to FIG. 6, it turned out that the voltage E between terminals was stable also in the case that the KCl aqueous solution is extremely dilute. In addition, according to FIG. 7, it turned out that the logarithm (log a) of the ionic activity and the voltage between terminals (E) showed a linear relationship in a broad range of the ionic activity (concentration). Since the response is generated due to Ag/AgCl electrode in the sample solution making a Nernst response to the activity of Cl⁻ in the sample solution, the result showed that the voltage difference at the interface between hydrophobic ionic liquid and the sample solution was constant in a broad range of the activity of potassium chloride.

<Embodiment 2>

Next, an embodiment 2 of measurement of the voltage between terminals by a model system using the reference electrode of the present claimed invention will be shown.

Figure 8:
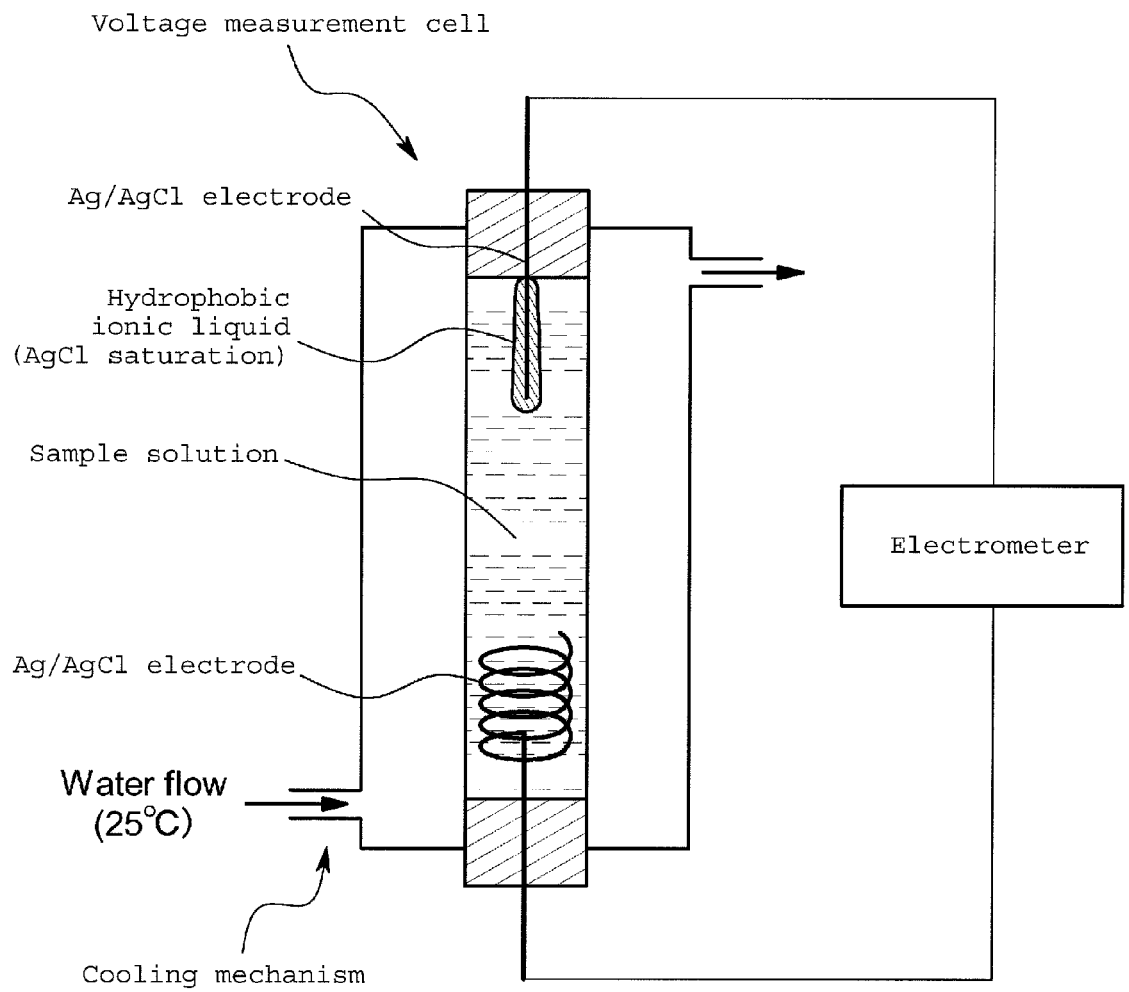
FIG. 8 is a pattern diagram showing a model system in accordance with an embodiment 2 of this invention.

The model system of this embodiment comprises, as shown in FIG. 8, a voltage measurement cell and an electrometer that measures a voltage E between terminals of the voltage measurement cell. The voltage measurement cell is so arranged that a distal end portion of an Ag/AgCl electrode is covered by a gelled hydrophobic ionic liquid and the distal end portion is inserted into the sample solution, and an ordinary Ag/AgCl electrode is inserted into the sample solution. In this embodiment, similar to the above-mentioned embodiment, the hydrophobic ionic liquid is C8mimC1C1N, and gelled by vinylidene fluoride-hexafluoropropylene copolymer. In addition, AgCl is contained in a saturated state in the hydrophobic ionic liquid.

In accordance with the model system having the above arrangement, a voltage E between terminals was measured by changing a concentration x of the sample solution according to x=10, 20, 50 mM with the sample solution being a KCl aqueous solution.

Figure 9:
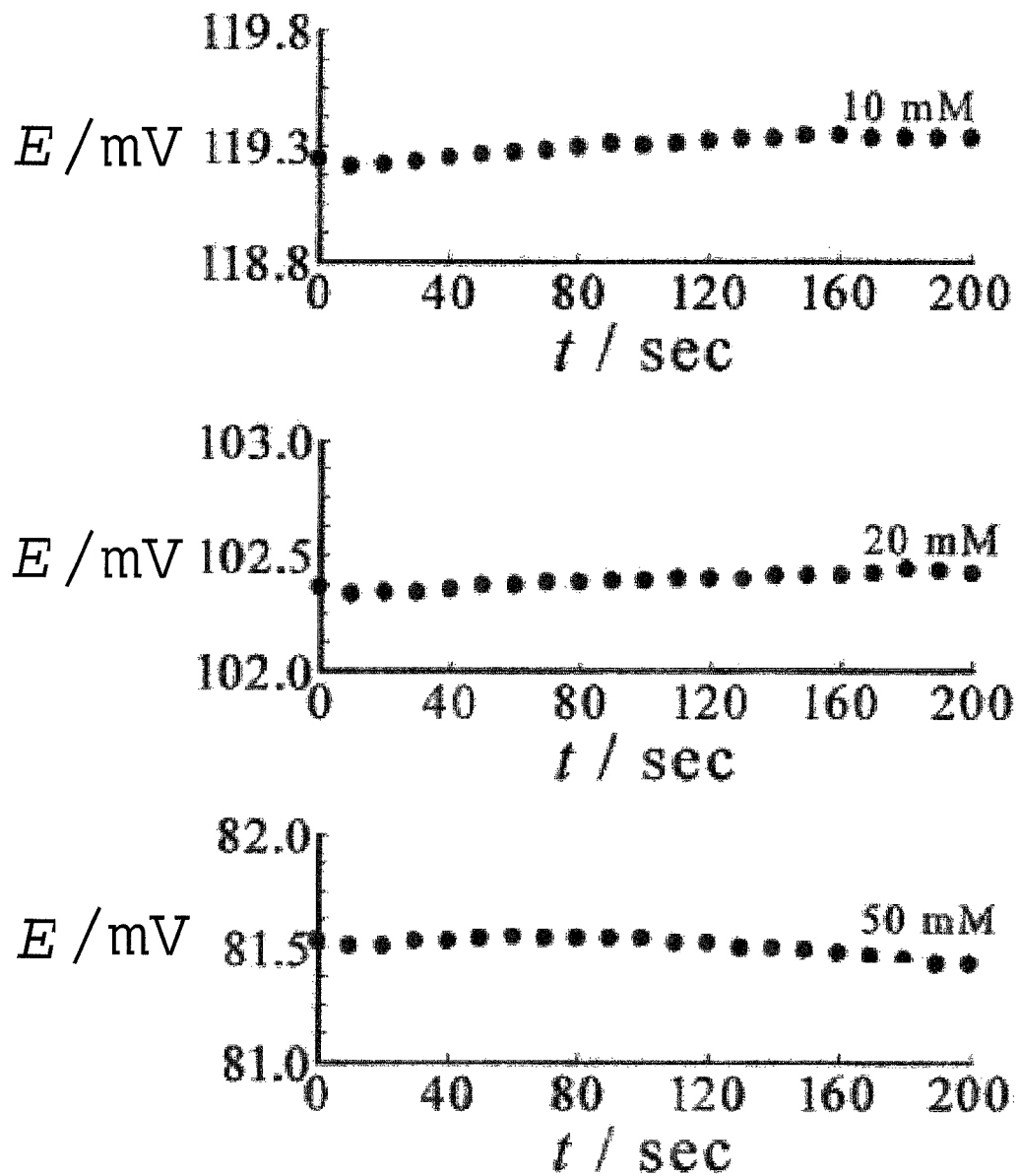
FIG. 9 is a diagram showing a time series change in a short period of time of a voltage between terminals recorded in case that the KCl concentration in the sample solution is 10 mM, 20 mM and 50 mM respectively in this embodiment.

The results are shown in FIG. 9. FIG. 9 shows a time series change of the voltage E between terminals for each above-mentioned concentration in a short period of time. According to FIG. 9, the voltage shown by the reference electrode of this invention was stable from immediate after the initiation.

Next, similarly to the above-mentioned embodiment 1, the voltage E between terminals was measured by changing a concentration x of the KCl aqueous solution according to x=1, 2, 5, . . . , 2000 mM.

Figure 10:
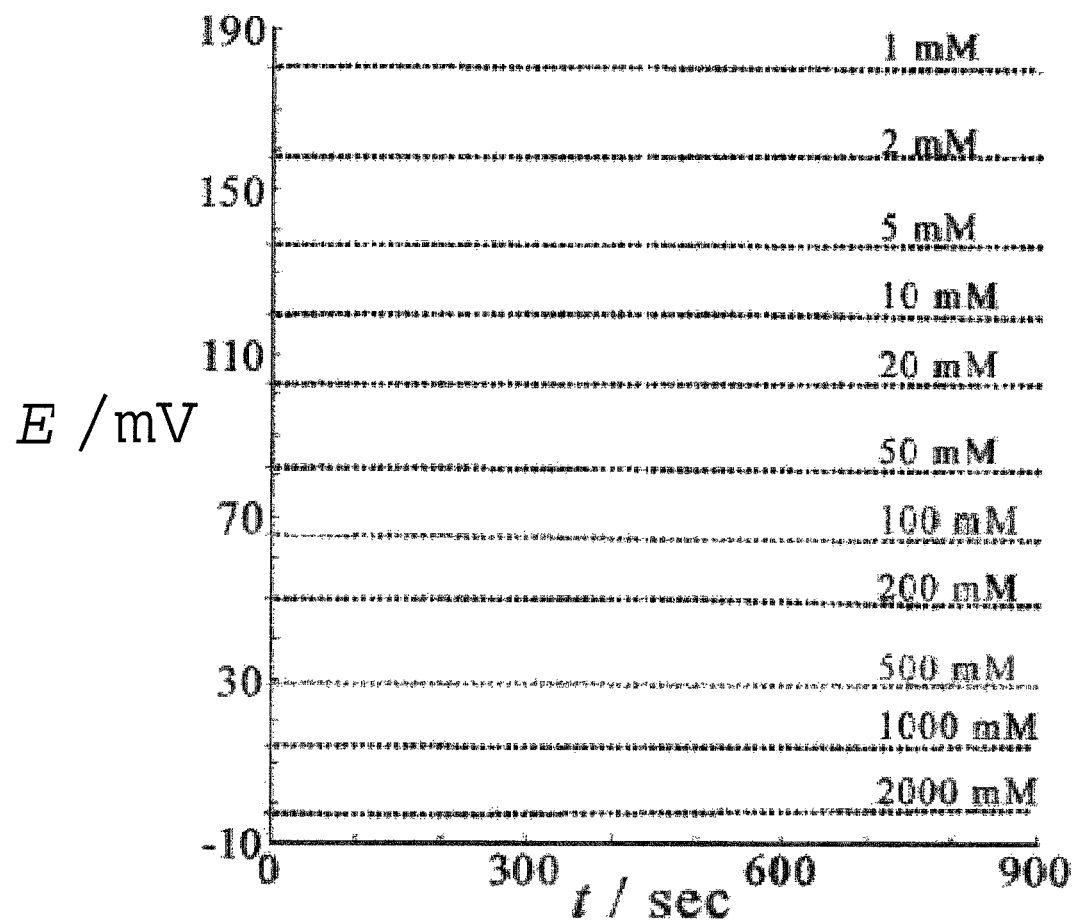
FIG. 10 is a diagram showing a time series change of a voltage between terminals recorded by changing the KCl concentration in the sample solution from 1 mM to 2000 mM in this embodiment.
Figure 11:
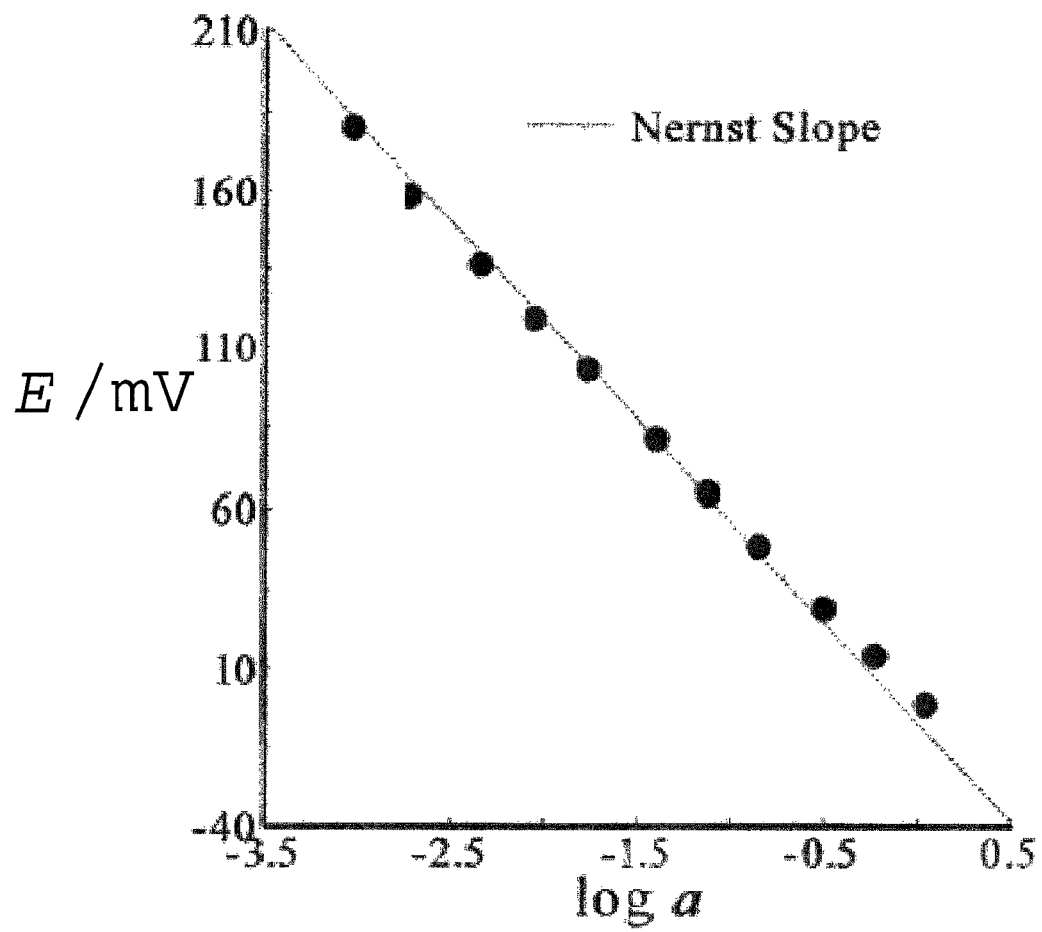
FIG. 11 is a view showing a result of the voltage between terminals, recorded by changing the KCl concentration in the sample solution from 1 mM to 2000 mM, plotted on the logarithm of the average ionic activity of the KCl concentration.

The results are shown in FIG. 10 and FIG. 11. FIG. 10 is a view showing the voltage E between terminals at a time when the concentration x of the KCl aqueous solution is changed according to x=1, 2, 5, . . ., 2000 mM, and FIG. 11 is a view showing a result of the voltage E between terminals plotted on the logarithm of an average ionic activity of KCl in the sample solution. According to FIG. 10, it turned out that the voltage E between terminals was stable in a broad range of the concentration also in the case of using the gelled hydrophobic ionic liquid. In addition, according to FIG. 11, it turned out that the logarithm (log a) of the ionic activity and the voltage E between terminals showed a linear relationship in a broad range of the ionic activity (concentration). Since the response is generated due to Ag/AgCl electrode in the sample solution making a Nernst response to the activity of Cl— in the sample solution, the result showed that the voltage difference at the interface between hydrophobic ionic liquid and the sample solution was constant in a broad range of the activity of potassium chloride.

Similarly, the voltage E between terminals was measured for the concentration x of the KCl aqueous solution as being the sample solution in accordance with x=20, 50, 100, 200, 500 μM.

Figure 12:
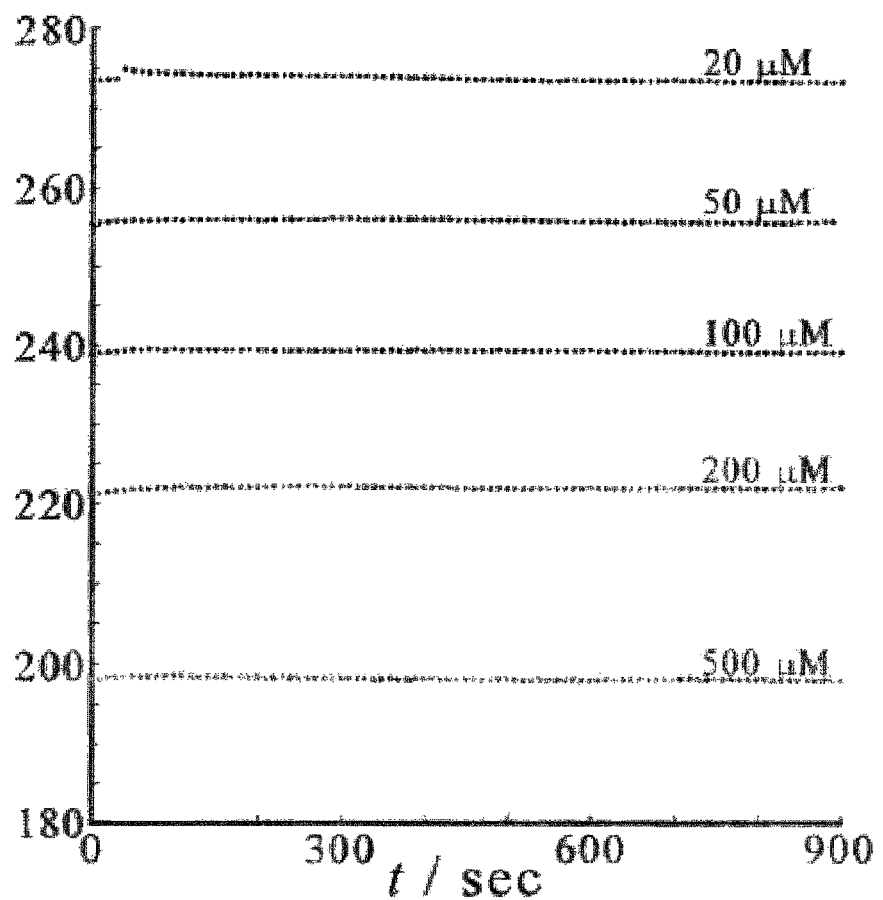
FIG. 12 is a diagram showing a time series change of the voltage between terminals recorded by changing the KCl concentration in the sample solution from 20 μM to 500 μM in this embodiment.
Figure 13:
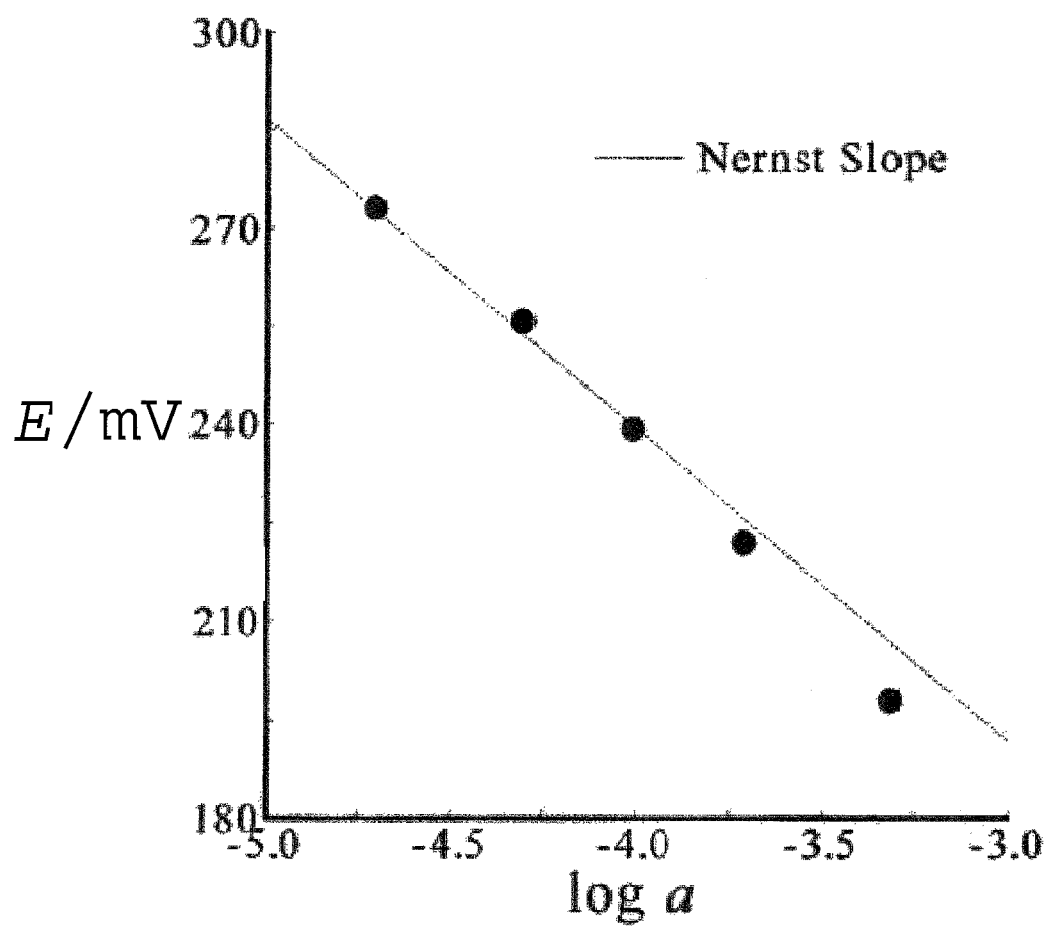
FIG. 13 is a view showing a result of the voltage between terminals, recorded by changing the KCl concentration in the sample solution from 20 μM to 500 μM, plotted on the logarithm of the average ionic activity of the KCl concentration.

The results are shown in FIG. 12 and FIG. 13. FIG. 12 is a view showing the voltage E between terminals at a time when the concentration x of the KCl aqueous solution is changed according to x=20, 50, 100, 200, 500 μM, and FIG. 13 is a view showing a result of the voltage E between terminals plotted on the logarithm of an average ionic activity of KCl in the sample solution. Especially according to FIG. 12, it turned out that the voltage E between terminals was stable also even though the KCl aqueous solution is extremely dilute in the case of using the gelatinized hydrophobic ionic liquid. In addition, according to FIG. 13, it turned out that the logarithm (log a) of the ionic activity and the voltage between terminals (E) showed a linear relationship in a broad range of the ionic activity (concentration). Since the response is generated due to Ag/AgCl electrode in the sample solution making a Nernst response to the activity of Cl⁻ in the sample solution, the result showed that the voltage difference at the interface between hydrophobic ionic liquid and the sample solution was constant in a broad range of the activity of potassium chloride.

<Other Modified Embodiment>

The present claimed invention is not limited to the above-mentioned embodiments.

Figure 14:
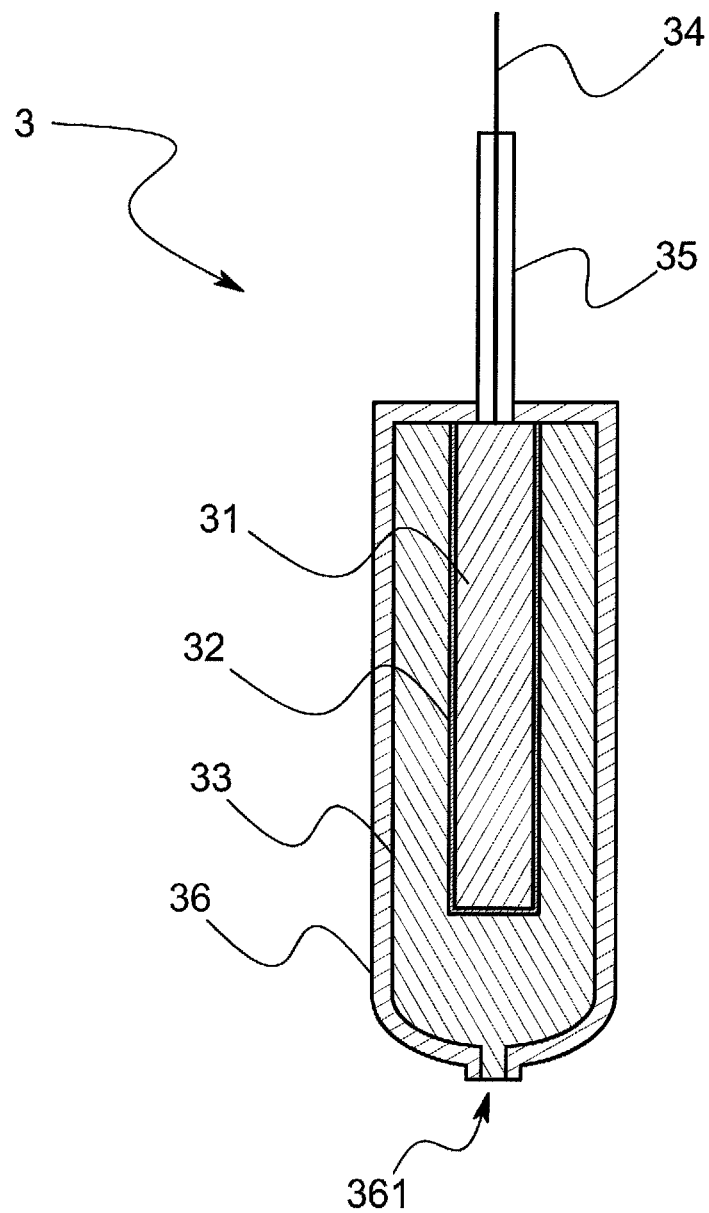
FIG. 14 is a cross-sectional view of the reference electrode in accordance with a modified embodiment of this invention.

For example, in the above-mentioned embodiment, it is possible to omit a sling tube if the gelled hydrophobic ionic liquid 33 is used, however, the hydrophobic ionic liquid 33 that is not gelled may be accommodated in a sling tube 36. In this case, as shown in FIG. 14, the reference electrode 3 comprises a metal body 31, a slightly soluble salt film 32 that covers the metal body 31 and that is made of a slightly soluble salt of the metal body 31, a hydrophobic ionic liquid 33 that is arranged to make contact with the slightly soluble salt film 32, and a sling tube 36 that accommodates the hydrophobic ionic liquid 33 and that has a junction 361 to make the hydrophobic ionic liquid 33 contact with the sample solution. In accordance with this arrangement, since the hydrophobic ionic liquid 33 that is extremely low-volatility at normal temperature is used without using an internal aqueous solution such as a KC1 solution, it is possible to make a space to accommodate the hydrophobic ionic liquid small, thereby downsizing the reference electrode 3.

The junction 361 in FIG. 14 is of a pinhole type, however, it may be of a ceramics type, a sleeve type or a double junction type. In addition, if the hydrophobic ionic liquid 33 is gelled, it is possible to further prevent the hydrophobic ionic liquid 33 from eluting out into the sample solution.

Figure 15:
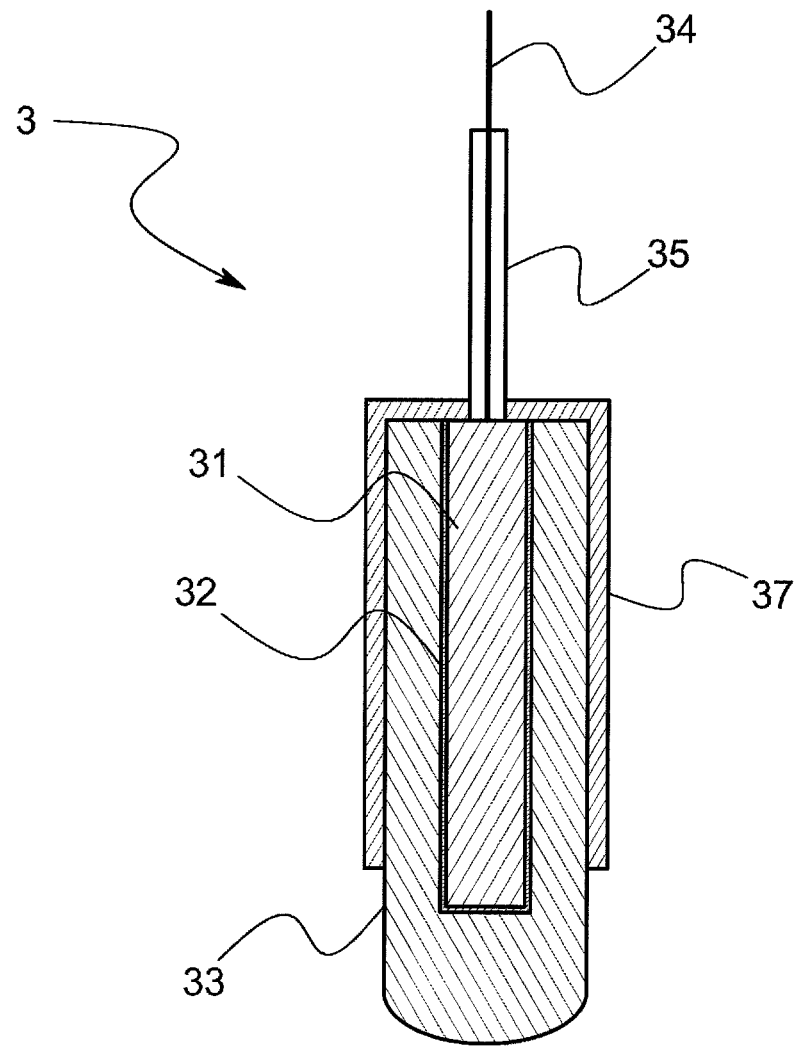
FIG. 15 is a cross-sectional view of the reference electrode in accordance with a modified embodiment of this invention.

Furthermore, as shown in FIG. 15, it can be conceived that the reference electrode may further comprise a holding member 37 that holds the hydrophobic ionic liquid 33 so as not to be exfoliated or separated from the slightly soluble salt film 32. The holding member 37 is to fix or support the gelled hydrophobic ionic liquid 33 on a circumference of the slightly soluble salt film 32, and may be, for example, a rough mesh film, a TEFLON (registered trademark) ring or a cylindrical glass tube. If they are used, the workability and the decay resistance can be further improved.

Figure 16:
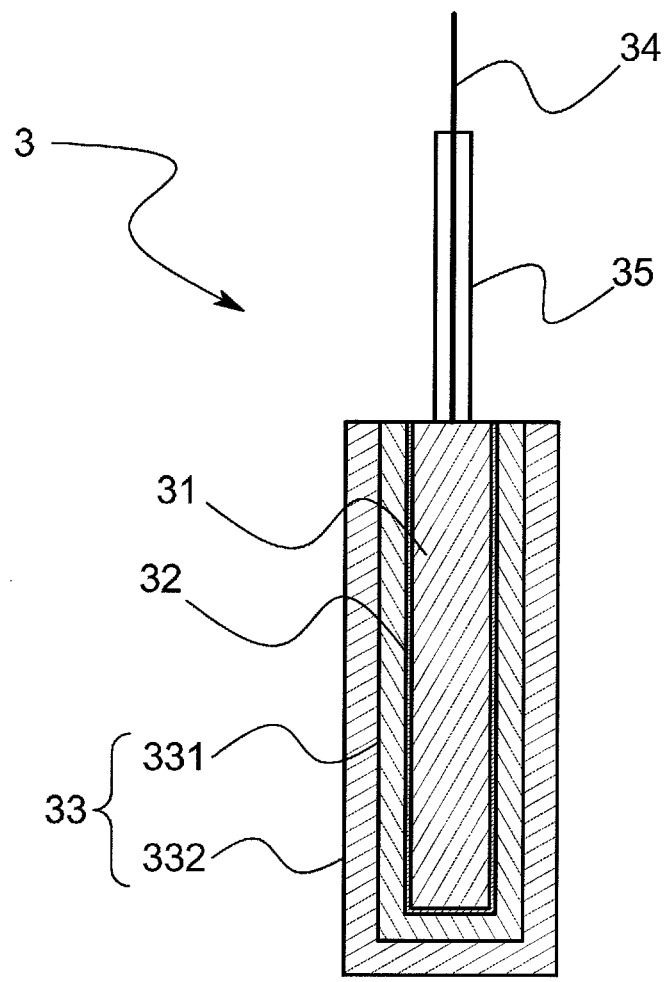
FIG. 16 is a cross-sectional view of the reference electrode in accordance with a modified embodiment of this invention.

In addition, as shown in FIG. 16, the hydrophobic ionic liquid 33 may be of a double structure. In other words, the hydrophobic ionic liquid 33 comprises an inside hydrophobic ionic liquid 331 that makes contact with the slightly soluble salt film 32 and an outside hydrophobic ionic liquid 332 that covers the inside hydrophobic ionic liquid 331, and the inside hydrophobic ionic liquid 331 comprises a slightly soluble salt in a saturated state and the outside hydrophobic ionic liquid 332 does not comprise the slightly soluble salt. Each of the hydrophobic ionic liquids 331, 332 is the same hydrophobic ionic liquid and gelled.

Figure 17:
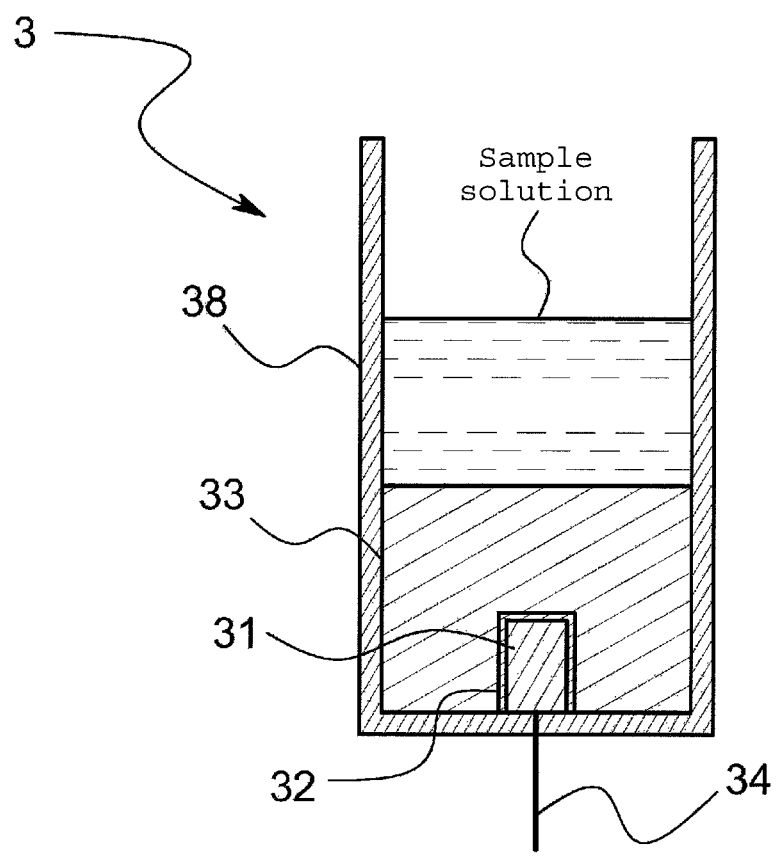
FIG. 17 is a cross-sectional view of the reference electrode in accordance with a modified embodiment of this invention.
Figure 18:
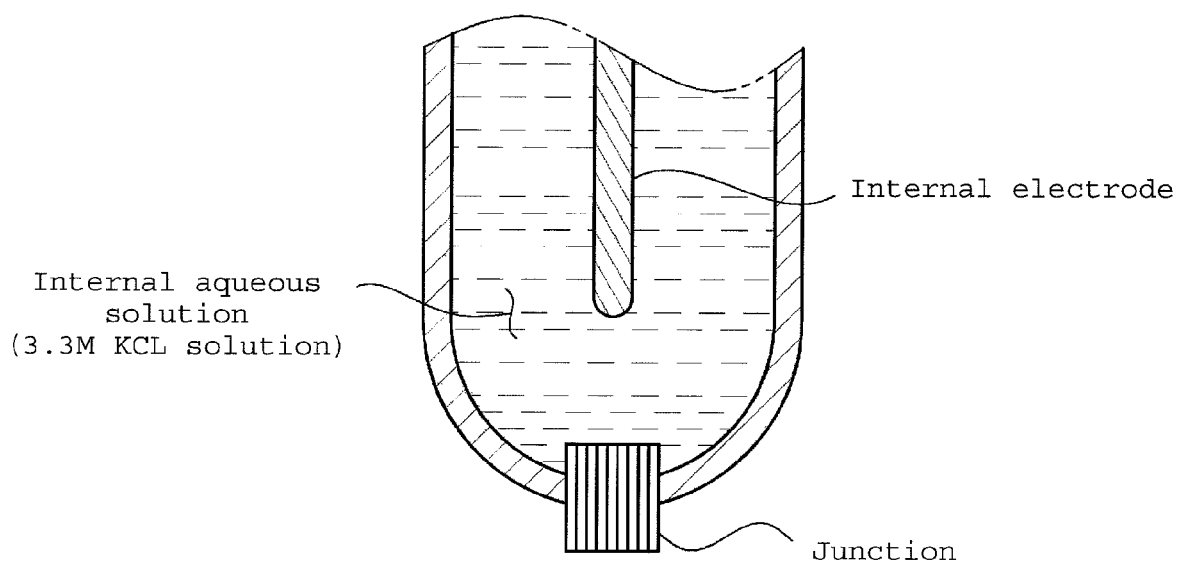
FIG. 18 is a partially enlarged cross-sectional view showing a conventional reference electrode.

Furthermore, as shown in FIG. 17, the reference electrode 3 may comprise a casing 38 having a bottom, a metal body 31 arranged to elongate inside from the bottom portion of the casing 38, a slightly soluble salt film 32 comprising a slightly soluble salt of the metal body 31 and covering the metal body 31 and a hydrophobic ionic liquid 33 arranged inside the casing 38 to make contact with the slightly soluble salt film 32. In this case, the electrochemical measurement is conducted by accommodating the sample solution over the hydrophobic ionic liquid 33 in the casing 38. In accordance with this arrangement, it is possible to provide a reference electrode of a solid type by gelatinizing or solidifying the hydrophobic ionic liquid 33.

In addition, the reference electrode may use a silver chloride sheet substrate with silver pattern plating. With this method, the reference electrode can be made flat and can be applied to a compact pH electrode if combined with a semiconductor manufacturing process.

Furthermore, the lead wire in the above-mentioned embodiment uses a conductive wire, however, may use a silver wire used for the metal body as it is.

In addition, the reference electrode of this invention is used for an ion concentration measurement system in the above-mentioned embodiment, however, in addition, it may be used also for an electrochemical measurement system such as, for example, a titration device, a polarographic device, an electroanalysis device, coulometric analysis device or a ORP device (oxidation-reduction potential measurement device).

Furthermore, it is possible to improve stability of an electric potential, a coating performance or a life duration of the electrode if a length of an alkyl chain is changed, or a combination is changed by using alkylphosphonium for a cation or $B(CN)_4^-$ or $B(CF_3)_4^-$ for an anion.

In addition, a part or all of the above-mentioned embodiment or the modified embodiment may be appropriately combined, and the present claimed invention is not limited to the above-mentioned embodiment and it is a matter of course that it can be variously modified without departing from its spirit.

Possible Applications In Industry

In accordance with this invention, it is possible to provide a reference electrode that has a merit of a salt bridge using a hydrophobic ionic liquid, that can stabilize an electric potential in a short period of time and that can be downsized.

The invention claimed is:
1. A reference electrode comprising:
a metal body,
a slightly soluble salt film that comprises a slightly soluble salt of the metal which constitutes the metal body and that coats at least a part of the metal body, and
hydrophobic ionic liquid that is arranged to cover the slightly soluble salt film and to make contact with both the slightly soluble salt film and a sample to be measured, without using an internal aqueous solution, wherein the hydrophobic ionic liquid is gelled and is substantially insoluble in water.

2. The reference electrode described in claim 1, wherein the hydrophobic ionic liquid comprises a cation and an anion for which standard Gibbs energy transferring between an ionic liquid and water is almost the same.

3. The reference electrode described in claim 1, wherein the hydrophobic ionic liquid contains the slightly soluble salt film in a saturated state.

4. The reference electrode described in claim 1, wherein the hydrophobic ionic liquid is gelled by a high polymer compound.

5. The reference electrode described in claim 4, wherein the high polymer compound is gum or resin.

6. The reference electrode described in claim 5, wherein the high polymer compound is at least one kind of a chemical compound selected from a group comprising vinylidene fluoride-hexafluoropropylene copolymer, polymethylmethacrylate, polyacrylonitrile, polybutylacrylate, and a derivative of polytetrafluoroethylene.

7. The reference electrode described in claim 1, wherein the hydrophobic ionic liquid comprises:
a cation that is at least one or more of a quaternary ammonium cation, quaternary phosphonium cation or quaternary alzonium cation, and
an anion including at least one or more of $[R_1SO_2NSO_2R_2]^-$ (each of $R_1$ and $R_2$ is a perfluoroalkyl group with a carbon number that is 1-12 respectively), a borate ion containing fluorine, $B(CN)_4^-$ (tetracyanoborate), bis(2-ethylhexyl)sulfosuccinate, $P(C_nF_{2n+1})_3F_3^-$, $(CF_3SO_2)_3C^-$, $AsF_6^-$, $SbF_6^-$, $(C_nF_{2n+1})SO_3^-$, or $(C_nF_{2n+1})COO^-$.

8. The reference electrode described in claim 7, wherein the cation is at least one or more of:

[Chemical formula 1]

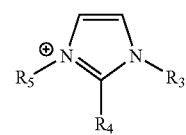

(1)

wherein $R_3$, $R_4$, or $R_5$ in the chemical formula 1 represent an alkyl group with a carbon number that is 1-12, a phenyl group or a benzyl group, and the alkyl group may contain a hetero atom;

[Chemical formula 2]

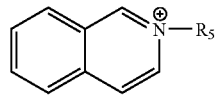
(2)

wherein $R_6$ in the chemical formula 2 represents an alkyl group with a carbon number that is 12-18, and the alkyl group may contain a hetero atom;

[Chemical formula 3]

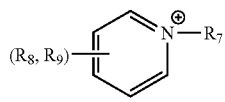
(3)

wherein $R_7$ in the chemical formula 3 represents an alkyl group with a carbon number that is 12-18, and the alkyl group may contain a hetero atom, and in addition, $R_8$, $R_9$ represent a hydrogen or methyl group;

[Chemical formula 4]

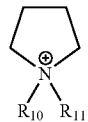
(4)

wherein $R_{10}$, $R_{11}$ in the chemical formula 4 represent an alkyl group with a hydrogen or carbon number that is 1-12, and the alkyl group may contain a hetero atom;

[Chemical formula 5]

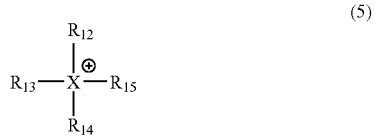
(5)

wherein $R_{12}$, $R_{13}$, $R_{14}$, $R_{15}$ in the chemical formula 5 represent an alkyl group with a carbon number that is 1-12, a phenyl group or a benzyl group, wherein the alkyl group may contain a hetero atom, and in addition, wherein X represents nitrogen, phosphorus or arsenic; or

[Chemical formula 6]

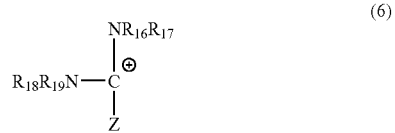
(6)

wherein in the chemical formula 6, $R_{16}$, $R_{17}$ represent an alkyl group with a hydrogen or carbon number that is 1-12, $R_{18}$, $R_{19}$ represent an alkyl group with a hydrogen or carbon number that is 1-12, and in addition, Z represents $NR_{20}R_{21}$, $OR_{22}$ or $SR_{23}$, and wherein $R_{20}$, $R_{21}$, $R_{22}$, $R_{23}$ represent an alkyl group with a carbon number that is 1-12.

9. An electrochemical measurement system using the reference electrode described in claim 1.

* * * * *

UNITED STATES PATENT AND TRADEMARK OFFICE
CERTIFICATE OF CORRECTION

PATENT NO. : 8,486,246 B2
APPLICATION NO. : 12/441370
DATED : July 16, 2013
INVENTOR(S) : Takashi Kakiuchi et al.

It is certified that error appears in the above-identified patent and that said Letters Patent is hereby corrected as shown below:

Title Page, Item 74, delete "Allenman" and insert --Alleman--.

In the Claims

At Column 15, line 7, delete Chemical Formula 2, and replace with Chemical Formula 2, as shown below.

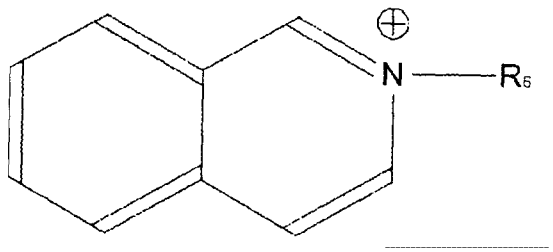

Signed and Sealed this
First Day of October, 2013

Teresa Stanek Rea
*Deputy Director of the United States Patent and Trademark Office*